US00PP11578P

United States Patent [19]

Lemon

[11] Patent Number: Plant 11,578

[45] Date of Patent: Oct. 17, 2000

[54] REGAL PELARGONIUM PLANT NAMED 'EXCALIBUR'

[75] Inventor: David G. Lemon, Lompoc, Calif.

[73] Assignee: Oglevee, Ltd., Connellsville, Pa.

[21] Appl. No.: 09/162,743

[22] Filed: Sep. 29, 1998

[51] Int. Cl.[7] ..... A01H 5/00

[52] U.S. Cl. ..... Plt./331

[58] Field of Search ..... Plt./331

[56] References Cited

U.S. PATENT DOCUMENTS

P.P. 10,000 8/1997 Lemon ..... Plt./331

P.P. 10,019 9/1997 Lemon ..... Plt./331

*Primary Examiner*—Howard J. Locker
*Assistant Examiner*—Wendy A. Baker
*Attorney, Agent, or Firm*—Webb Ziesenheim Logsdon Orkin & Hanson, P.C.

[57] ABSTRACT

'Excalibur' is a new regal geranium variety which is added to the "Royalty" regal geranium series to replace 'Duchess'. Flower color is slightly different than 'Duchess' and the floret size is larger. Cutting production and rooting speed are equal to or better than 'Duchess'. Plant habit is slightly shorter and well branched. The finished plant habit is slower to shatter than most plants of the species, lasting up to three weeks or more in the home.

1 Drawing Sheet

BACKGROUND OF THE INVENTION

This discovery relates to a new and distinct variety of *Pelargonium×domesticum* identified by the varietal name of 'Excalibur', Breeder No. 4DG663 and Oglevee, Ltd. No. 88. The new variety was discovered by David G. Lemon in a selected breeding program in Connellsville, Pa. The new variety is a selection from the crossing of a breeding variety, Oglevee, Ltd. No. 335 (unpatented) and the commercial variety 'Josy', U.S. Plant Pat. No. 6,019. It was first asexually reproduced on Aug. 14, 1995 at Oglevee, Ltd. in Connellsville, Pa. and has been found to retain its distinctive characteristics through successive generations.

The new variety, was grown in a glass greenhouse in Connellsville, Pa. using full light, 60° F. night temperature and 68° F. day temperature and grown in a soilness media with constant fertilizer at 150–200 ppm nitrogen and potassium, has a response time of seventeen weeks to flowering from a rooted cutting potted in a 6 inch pot. Rooted cuttings potted Oct. 15, 1997 flowered Feb. 9, 1998.

DESCRIPTION OF THE DRAWING

The accompanying photographic drawing illustrates the new variety, with the color being as nearly true as is possible with color illustrations of this type.

DESCRIPTION OF THE NEW PLANT

The following detailed descriptions set forth the characteristics of the new variety. The data which define these characteristics were collected from asexual reproductions carried out at Oglevee, Ltd., 152 Oglevee Lane, Connellsville, Pa. 15425. The color readings on a test plant grown in a 13 cm pot were taken indoors at 200–220 foot candles of cool white fluorescent light. Color references are primarily to The R.H.S. Colour Chart of The Royal Horticultural Society of London.

THE PLANT

Classification:
- *Botanical.*—*Pelargonium×domesticum.*
- *Varietal.*—Regal geranium named 'Excalibur'.

Form: Upright medium mound habit.
Height: 20–23 cm above top of pot.

Growth: Free basal branching; medium plant habit.
Strength: Does not require artificial support.
Rooting speed: Cuttings produce 3 to 5 roots visible to outside of artificial growing media in 14 to 16 days.
Foliage: Stalked leaf attachment.
Leaves:
- *Size.*—11.0–12.0 cm fuilly expanded.
- *Shape.*—Depressed ovate; truncate base.
- *Margin.*—Serrately lobed.
- *Texture.*—Pubescent, leathery.
- *Color.*—Top: Green Group 137C. Bottom: Green Group 138B. Zone: None.
- *Ribs and veins.*—Venation: Palmate. Color: Yellow-Green Group 147C.

Petioles:
- *Length.*—5.8–9.3 cm.
- *Color.*—Yellow-Green Group 146B.

Stem:
- *Color.*—Yellow-Green Group 146C. p2 *Internode length.*—2.5–3.5 cm.

THE BUD

Shape:
- *Overall.*—Elliptical cluster when no color showing.
- *Individual buds.*—Elliptical or oval when no color showing.

Size: 3.0–4.0 cm across.
Number of buds per cluster: 11–14.

INFLORESCENCE

Blooming habit: Medium sized florets forming full flower head; 11–14 florets per umbel; continuous flowering.
Borne: Umbel, flowers on pedicel, pedicel on peduncle, peduncles are 0.5–1.5 cm above foliage.
Closed florets:
- *Size.*—2.0–3.0 cm long, 1.0 cm wide when just showing color.

Open florets:
- *Form.*—Slightly cupped, slightly ruffled edges.
- *Size of fully open bloom.*—Umbel: 6.0–7.0 cm across. Floret: 2.5–3.7 cm wide; 4.0–4.8 cm long.
- *Color.*—Top: Top two petals have an eye of Red Group 53B shading to Red Group 48C in the middle with an edge of Red Group 55D. Veining is Red-Purple Group 59A shading to Red-Purple Group 64A. Lower three petals have a smaller eye of Red Group 48C shading to a larger area in the middle and edge of Red Group 55D. Veining is Red-Purple Group 59A shading to Red-Purple Group 64A is still present, but not as prominent as on the top two petals. Bottom: Red Group 56D with eye and veining showing through. Eye: Present.

*Petals*.—5–6 in number.

Texture and appearance: Satiny, slightly reflective.

Tonality from a distance: Light pink flowers with an orange-red eye above medium green foliage.

Petaloids: None.

Pedicel:

*Length*.—2.5–3.0 cm.

*Color*.—Yellow-Green Group 146B.

Peduncle:

*Length*.—5.0–7.0 cm.

*Color*.—Yellow-Green Group 146B.

Disease resistance: No unusual susceptibility to diseases of Pelargonium has been observed.

Lasting quality: Continuous blooming; slow to shatter, overall plant bloom lasts 14–21 days when brought into the home as a flowering pot plant.

REPRODUCTIVE ORGANS

Stamens:

*Anthers*.—4 mm long.

*Filaments*.—7–10 mm long; white in color.

*Pollen color*.—Orange to orange red; very little present.

Pistils:

*Number*.—1.

*Length*.—2.4–2.6 cm.

*Stigma color*.—Red-Purple Group 59A.

*Style*.—1.3–1.5 cm long.

*Ovaries*.—Pale green; superior; pubescent; 6 mm long.

Fruit: None observed.

GENERAL CHARACTERISTICS

The new variety is an addition to the "Royalty" regal geranium series. Flower color is slightly different than 'Duchess' (U.S. Plant Pat. No. 8,704) and the floret size is larger. Cutting production and rooting speed are equal to or better than 'Duchess'. The new variety exhibits smaller repeatedly blooming flowers than the seasonally produced flowers of the parent cultivar 'Josy'. The color pattern of 'Excalibur' is more distinct with a heavier streak of red than in 'Josy'. Plant habit is slightly shorter and well branched. The finished plant habit is slower to shatter of the inflorescence than most plants of the species (particularly when exposed to ethylene), lasting up to three weeks or more in the home. This variety has been successfully trialed.

I claim:

1. A new and distinct variety of geranium plant named 'Excalibur' as described and illustrated herein.

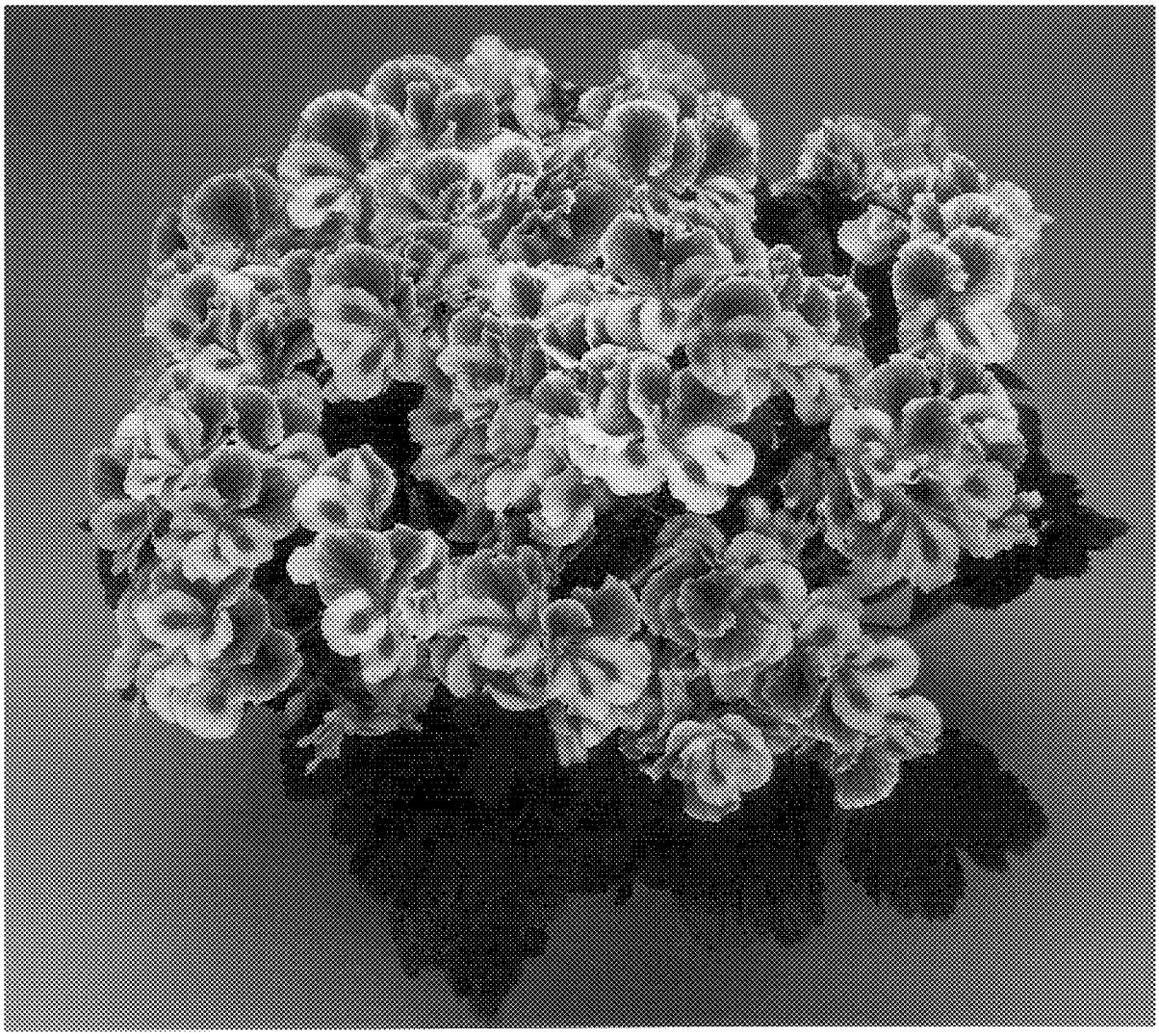

* * * * *